US00PP36495P2

(12) United States Plant Patent
Chelednik

(10) Patent No.: US PP36,495 P2
(45) Date of Patent: Feb. 25, 2025

(54) ***CAMELLIA* PLANT NAMED 'Gordon's Flash'**

(50) Latin Name: *Camellia japonica*
Varietal Denomination: 'Gordon's Flash'

(71) Applicant: Michael Edmund Chelednik, Fuquay-Varina, NC (US)

(72) Inventor: Michael Edmund Chelednik, Fuquay-Varina, NC (US)

( * ) Notice: Subject to any disclaimer, the term of this patent is extended or adjusted under 35 U.S.C. 154(b) by 0 days.

(21) Appl. No.: 18/799,979

(22) Filed: Aug. 9, 2024

Related U.S. Application Data

(60) Provisional application No. 63/539,078, filed on Sep. 18, 2023.

(51) Int. Cl.
*A01H 6/00* (2018.01)
*A01H 5/02* (2018.01)

(52) U.S. Cl.
USPC ..... Plt./243

(58) Field of Classification Search
USPC ..... Plt./243
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Camellia japonica* plant named 'Gordon's Flash' that is characterized by its variegated foliage with a wide margin of yellow to pale yellow and green centers, its very vigorous growth habit; unique for having variegated foliage, its good early branching, and its peony-formed flowers that are maroon red in color with gold stamens.

2 Drawing Sheets

Botanical classification: *Camellia japonica.*
Variety denomination: 'Gordon's Flash'.

BACKGROUND OF THE INVENTION

The present invention relates to a new and distinct cultivar of *Camellia* plant, botanically known as *Camellia japonica*, 'Gordon's Flash'. The new cultivar will be referred to hereafter by its cultivar name, 'Gordon's Flash'. 'Gordon's Flash' is a new evergreen shrub grown for container and landscape use.

The Inventor discovered the new cultivar in April of 2004 as a naturally occurring branch mutation of *Camellia japonica* 'Maroon and Gold' (not patented) that was growing in a garden in Arnaudville, Louisiana.

Asexual propagation of the new cultivar was first accomplished by stem cuttings under the direction of the Inventor in 2019 in Wendell, North Carolina. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia*. These attributes in combination distinguish 'Gordon's Flash' as a new and distinct cultivar of *Camellia.*

1. 'Gordon's Flash' exhibits variegated foliage with a wide margin of yellow to pale yellow and green centers.
2. 'Gordon's Flash' exhibits a very vigorous growth habit; unique for having variegated foliage.
3. 'Gordon's Flash' exhibits good early branching.
4. 'Gordon's Flash' exhibits peony-formed flowers that are maroon red in color with gold stamens.

The parent plant of 'Gordon's Flash' differs from 'Gordon's Flash' in having foliage that is non-variegated. 'Gordon's Flash' can also be compared to the *Camellia japonica* cultivars 'Geoff Hamilton' (not patented) and 'Taiyo' (not patented). 'Geoff Hamilton' is similar to 'Gordon's Flash' in having a variegated foliage with yellow margins. 'Geoff Hamilton' differs from 'Gordon's Flash' in having foliage margins that are less bright in color and in a much less vigorous growth habit. 'Taiyo' is similar to 'Gordon's Flash' in having an variegated foliage. 'Taiyo' differs from 'Gordon's Flash' in having foliage in which the variegation is central and blotchy rather than marginal, a much less vigorous growth habit, and a plant habit that is less compact.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include a website listing by Garden Treasures Nursery.

BRIEF DESCRIPTION OF THE DRAWINGS

The accompanying colored photographs illustrate the overall appearance and distinct characteristics of the new *Camellia.*

The photograph in FIG. 1 was taken of a 18-month-old-plant of 'Gordon's Flash' as grown in a greenhouse in a 2-quart container in Wendell, North Carolina and provides a view of the foliage of 'Gordon's Flash'.

Figure 1:
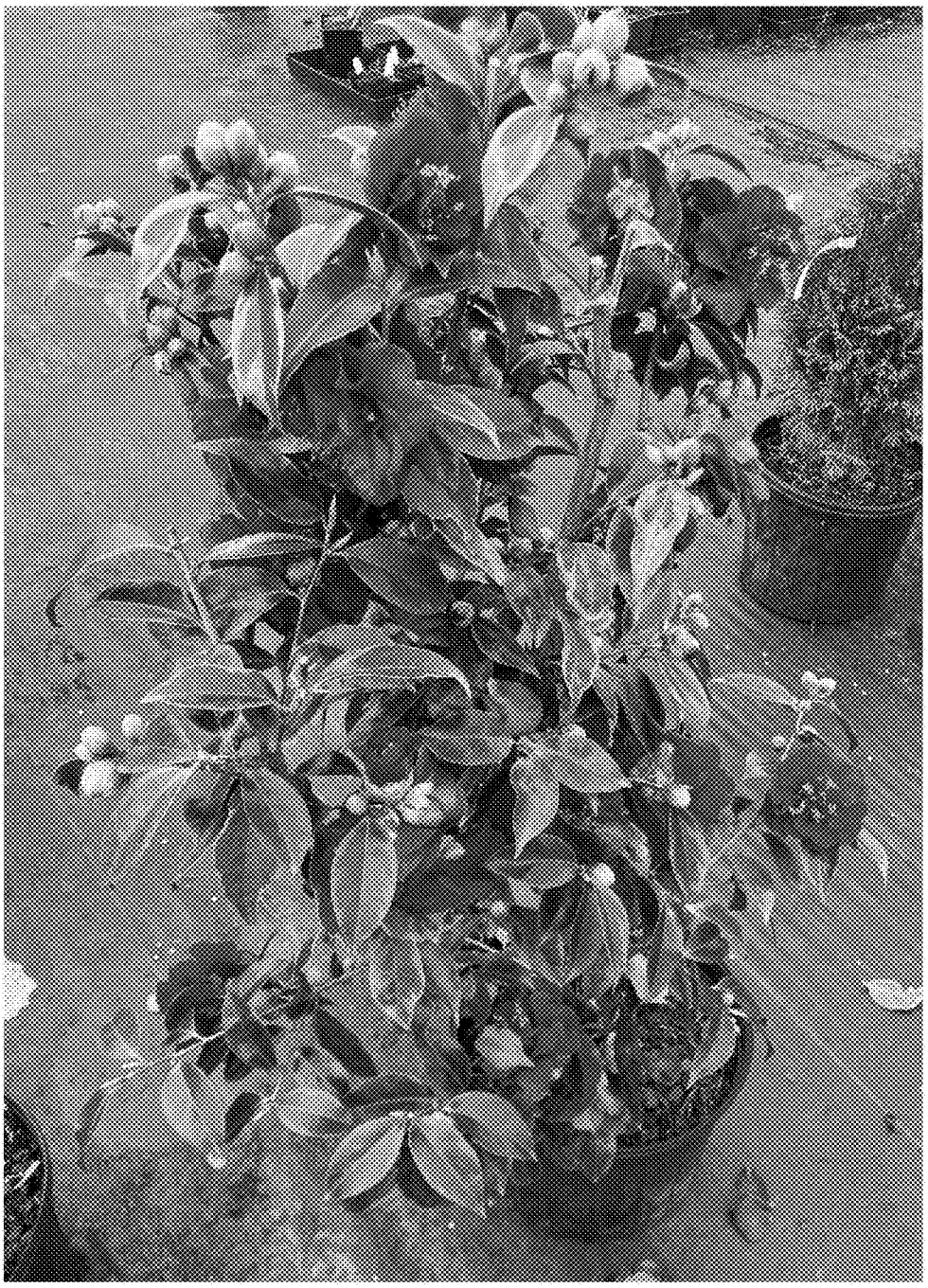
Figure 2:
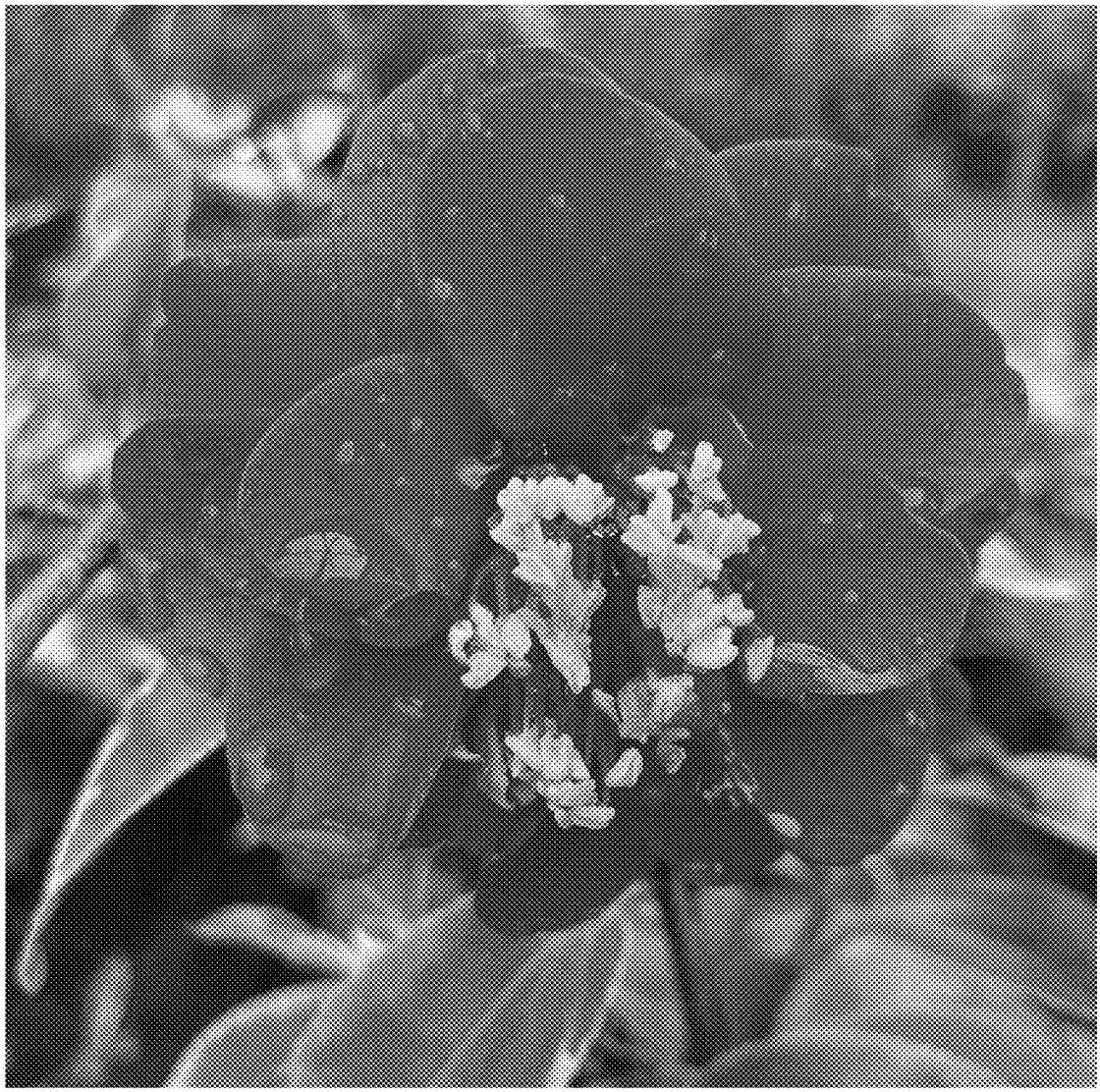

The photograph in FIG. 2. was taken of a 18-month-old-plant of 'Gordon's Flash' as grown in a greenhouse in a 2-quart container in Wendell, North Carolina and provides a close-up view of a flower of 'Gordon's Flash'.

The colors in the photograph are as close as possible with digital photography techniques available, the color values cited in the detailed botanical description accurately describe the colors of the new *Camellia*.

DETAILED BOTANICAL DESCRIPTION

The following is a detailed description of 18-month-old plants of the new cultivar as grown in a greenhouse in 2-quart containers in Wendell, North Carolina. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit*.—Late February through March in central North Carolina.

*Plant type*.—Evergreen shrub.

*Plant habit*.—Upright, bushy, early branching.

*Height and spread*.—An average of 2.4 m in height and 1.2 m in spread when mature in the landscape.

*Hardiness*.—At least hardy in U.S.D.A. Zones 7b to 9a.

*Diseases and pests*.—Has been observed to be disease free, however no susceptibility or resistance to specific diseases or pests has been observed.

*Propagation*.—Stem cuttings.

*Time required for root initiation*.—30 to 45 days.

*Time required for root development*.—About 6 months to fully develop a small, young plant from a rooted cutting.

*Growth rate*.—Vigorous.

*Root description*.—Fine, freely branched, 174A.

Branch description:

*Branch shape*.—Round.

*Branch strength*.—Strong.

*Branch color*.—Young; 144A, older; 160D, lightly flushed with 178A, mature and bark; a blend of 177A, 200B, and 164B.

*Branch size*.—Main; an average of 31 cm in length and 1 cm in diameter, lateral; 20 cm in length, 4 mm in diameter, tertiary; 2 cm in length, 2 mm in diameter.

*Branch surface*.—Young and older; glabrous, glossy, sheen, mature and bark; exfoliating, matte.

*Branching*.—Main; 1, lateral; 8 per main, tertiary; 4 per lateral.

Foliage description:

*Leaf shape*.—Elliptic.

*Leaf division*.—Simple.

*Leaf base*.—Cuneate.

*Leaf apex*.—Acuminate to acute.

*Leaf fragrance*.—None.

*Leaf margins*.—Serrate.

*Leaf arrangement*.—Alternate.

*Leaf attachment*.—Petiolate.

*Leaf substance*.—Thick and rubbery.

*Leaf surface*.—Both surfaces very glossy, glabrous, moderately wavey.

*Leaf size*.—An average of 8 cm in length and 3.5 cm in width.

*Leaf aspect*.—Held in various angles, slightly recurved.

*Leaf quantity*.—An average of 50 per plant.

*Leaf venation*.—Pinnate, inconspicuous except for upper mid-rib; 144A.

*Leaf variegation*.—Moderate, inconsistant.

*Leaf color*.—Emerging upper and lower surface; variegated, centers 177A, edges 155A, strongly suffused with 68A and 70D, as the foliage matures they lose the pink colorations, young upper and lower surface; variegated, centers 144B, edges 157D and NN155D, mature leaves upper and lower surface; variegated, centers 139A and 139B, edges 138A and 138B.

*Leaf buds*.—Lanceolate in shape, an average of 1.5 cm in length and 4 mm in width, 144A in color, very glossy and glabrous surface.

*Stipules*.—None.

Inflorescence description:

*Inflorescence type*.—Solitary.

*Flower number*.—An average per lateral branch; 1 fully open flower and 12 buds.

*Flower fragrance*.—Faint, similar to a rose fragrance.

*Flower longevity*.—Average of one week, self cleaning.

*Flower type*.—Rotate, single.

*Flower aspect*.—Outward and slightly upright.

*Flower size*.—An average of 8.5 cm in diameter and 5 cm in depth.

*Peduncles*.—None, flowers are sessile to stem.

*Flower buds*.—Young buds ovate in shape, before burst becoming round in shape, an average of 2.3 cm in length and 1.5 cm in width, color; a blend 59A and 60A in color, surface is moderately glossy with a translucent sheen, terminal arrangement.

*Sepals*.—An average of 6, ovate to oval in shape and strongly cupped inward, imbricate, an average of 2 cm in length and 1.8 cm in width, retuse to obtuse apex, obtuse base, entire to slightly undulate margins that are curled outwards, upper and lower surfaces moderately glossy, sheen and moderately rugose, slightly translucent, margins are very translucent, outer surface is densely covered with fine, very soft and velvety pubescence matching surface color, color: upper and lower surfaces; a blend of 145B and N144C, randomly flushed towards the base and center with 54C and 45A, margins 150D.

*Petals*.—An average of 25, obcordate to obovate in shape, sometimes obtuse in shape, an average of 4.5 cm in length and 3 cm width, apex is retuse to obtuse, base cuneate, margins slightly undulated, both surfaces are moderately glossy, velvety, slightly thick in texture, color: when opening upper and lower surface; a blend of 187C and 187A, when fully open upper and lower surface; 46A.

*Receptacle*.—Disk-shaped, 1 cm in diameter and 5 mm in depth.

Reproductive organs:

*Gynoecium*.—Pistils; up to 14, style; average of 1.4 cm in length, 1.5 mm in width, bases suffused to each other and around ovary, color; young styles 158C, lightly flushed at the base with 185A, mature styles 38D, base 53A, stigmas; 1 mm in diameter and depth, club-shaped, young stigmas 154B in color, mature stigmas N199A and 203A, ovary; superior, 1 cm in depth, 5 mm in width, oblong in shape, glossy and glabrous surface, 154A in color.

*Androecium*.—Stamens; an average of 35, sasangua arrangement, filaments; up to 3.5cm in length, round in shape, surface is satiny and glabrous, color; 54A, base 50A, anthers; an average of 2 mm in total length, 1 mm in depth, 22A in color, pollen; moderate in quantity, 22A in color.

*Fruit and seed*.—None observed to date.

It is claimed:

1. A new and distinct cultivar of *Camellia* plant named 'Gordon's Flash' as herein illustrated and described.

* * * * *